United States Patent [19]

Smith et al.

[11] Patent Number: 4,900,305
[45] Date of Patent: Feb. 13, 1990

[54] AMBULATORY INFUSION PUMP

[75] Inventors: Timothy J. N. Smith; Alois J. van Eyken; Charles A. Mulvenna, all of Kingston, Canada

[73] Assignee: Queen's University at Kingston, Kingston, Canada

[21] Appl. No.: 212,177

[22] Filed: Jun. 27, 1988

[51] Int. Cl.⁴ .................................................. A61M 5/00
[52] U.S. Cl. ........................................ 604/65; 604/131; 604/246; 604/249; 128/DIG. 12
[58] Field of Search ................... 604/118, 65, 67, 151, 604/131, 246, 249; 222/450; 121/DIG. 12, DIG. 13

[56] References Cited

U.S. PATENT DOCUMENTS 4,303,376 12/1981 Siekmann ............................ 604/249
4,411,651 10/1983 Schulman ............................ 604/246
4,596,558 6/1986 Smith et al. ........................ 604/134

Primary Examiner—Stephen C. Pellegrino
Attorney, Agent, or Firm—Richard J. Hicks

[57] ABSTRACT

A pulsed liquid injection device for injection of predetermined dosage volumes of medication at predetermined intervals of time over an extended period is described. A relatively large supply of medication is maintained in a bag under pressure, and metered portions thereof are released at time intervals by an electronically controlled metering device. The metering device includes a simple valve arrangement containing three flexible resilient elements arranged and controlled in such a way as to provide shut off of medication supply in the event of a malfunction, either electrical or mechanical.

19 Claims, 3 Drawing Sheets

AMBULATORY INFUSION PUMP

FIELD OF INVENTION

This invention relates to a drug delivery system, and more particularly to a miniaturized pressure system suitable for ambulatory use by a patient over a relatively long time frame.

CROSS REFERENCE TO RELATED APPLICATIONS

This application is related to our commonly assigned U.S. application Ser. No. 775,997 filed Sept. 13, 1985, and now U.S. Pat. No. 4,596,558 issued June 24, 1986.

BACKGROUND OF INVENTION

Over the past few years medical treatments have advanced dramatically and it is now possible to treat, on a continuous or at least semi continuous out-patient basis, various complaints and disorders which were previously not treatable at all or which required lengthy stays in hospital so that skilled personnel were available to administer relatively potent and possibly toxic drugs at prescribed time intervals. Various ambulatory medication infusion pumps have been developed over the years but most have been relatively bulky so that they cannot be worn discreetly beneath the clothes or have been relatively expensive. Efforts have, therefore, centred upon miniaturization and cost reduction. The problems of miniaturization have been largely solved by extensive use of solid state electronic devices to control and time the administration of dose amounts of the medication, by advances in battery technology which has reduced the size of the power source required and by the use of simple spring devices to provide a pressurized medication reservoir. Attention is directed to our earlier patent, U.S. Pat. No. 4,596,558 issued June 24, 1986 which describes such a miniature ambulatory medication infusion device. The cost of this device has been reduced relative to devices presently on the market by the simplification of parts and extensive use of polymeric materials for manufacture. Problems do, however, still remain with respect to the cost of disposable elements, reliability. simplicity of use and most importantly the provision of a multi mode fail-safe performance. In our prior device a three way valve is provided between a relatively large medication reservoir pressurized by means of a pair of external leaf springs and a smaller medication dispenser also pressurized by means of external leaf springs. The pressure in the medication reservoir is greater than the pressure in the medication dispenser, which in turn is greater than the venous pressure. In operation, the three way valve, which in the normal de-energized state blocks flow from the medication dispenser to the patient, is energized to open a passage from the medication dispenser to the patient while blocking the passage from the medication reservoir. As the pressure of the medication dispenser is greater than the venous pressure the dispenser discharges a metered dose intravenously or subcutaneously to the patient. Upon deactivation, the valve returns to the rest position with the patient passage blocked but the passage from the medication reservoir to the medication dispenser open. As the pressure in the reservoir exceeds that of the dispenser, the dispenser refills to capacity. The problem is that through spring or solenoid failure or the presence of foreign bodies in the system, it is conceivable that the three way valve could come to rest in an intermediate position in which none of the ports are properly sealed. This would lead to a condition known as streaming, in which medication would flow continuously and directly from the relatively large reservoir to the patient, with the obvious risk of a dangerous overdose, until the reservoir is completely voided or until some corrective action is taken.

OBJECT OF INVENTION

Thus, it is one object of the present invention to provide a low cost, ambulatory medication infusion device which has a multi mode fail-safe performance.

Another object of the present invention is to provide a low cost, disposable dosage metering chamber having normally closed valves which may be simply inserted into an ambulatory medication infusion device.

SUMMARY OF INVENTION

By one aspect of the invention there is provided a pulsed liquid injection device comprising:

a liquid storage container adapted to store liquid under a pressure greater than that required for making an injection:

a liquid metering chamber having a predetermined capacity and adapted to store liquid under a pressure which is greater than that required for making injections but lower than the pressure in said first storage container;

liquid dispensing means:

a first liquid flow path between said storage container and said metering chamber;

a second liquid flow path between said metering chamber and said liquid dispensing means:

first valve means in said first liquid flow path movable between a first operating position in which said first liquid flow path is blocked and a second operating position in which said first liquid flow path is open;

second valve means in said second liquid flow path movable between a first operating position in which said second liquid flow path is blocked and a second operating position is which said second liquid flow path is open: and timing means arranged, repeatedly at predetermined intervals, to (a) open said first valve means for first sufficient time to permit said liquid to flow into and fill said metering chamber and then return said first valve means to its first operating position, and subsequently (b) open said second valve means for sufficient time to permit a predetermined volume of said liquid in said metering chamber to flow to said liquid dispensing means and then return said second valve means to its first operating position.

In a preferred embodiment of this invention the device also includes means intermediate said first and second valve means arranged to block said second liquid flow path in the event that liquid in excess of said predetermined capacity of said metering chamber is delivered thereto.

By another aspect of the invention there is provided a valve arrangement adapted for addition to a pulsed liquid injection system, of which it then forms part, the arrangement comprising: a housing having a liquid flow path therethrough and containing a liquid metering chamber intermediate the ends thereof; first valve means in said flow path upstream of said metering chamber and second valve means in said flow path downstream of said metering chamber, said first and second valve means being operatively movable between respective first positions which block said flow path and second positions in which said flow path is open; and sensing means in said flow path operatively connected to third valve means arranged to block said liquid flow path in the event that in excess of a predetermined volume of liquid is exhausted from said metering chamber.

BRIEF DESCRIPTION OF DRAWINGS

The invention will be described in more detail hereinafter with reference to the accompanying drawings in which.

DETAILED DESCRIPTION OF PREFERRED EMBODIMENTS

Figure 1:
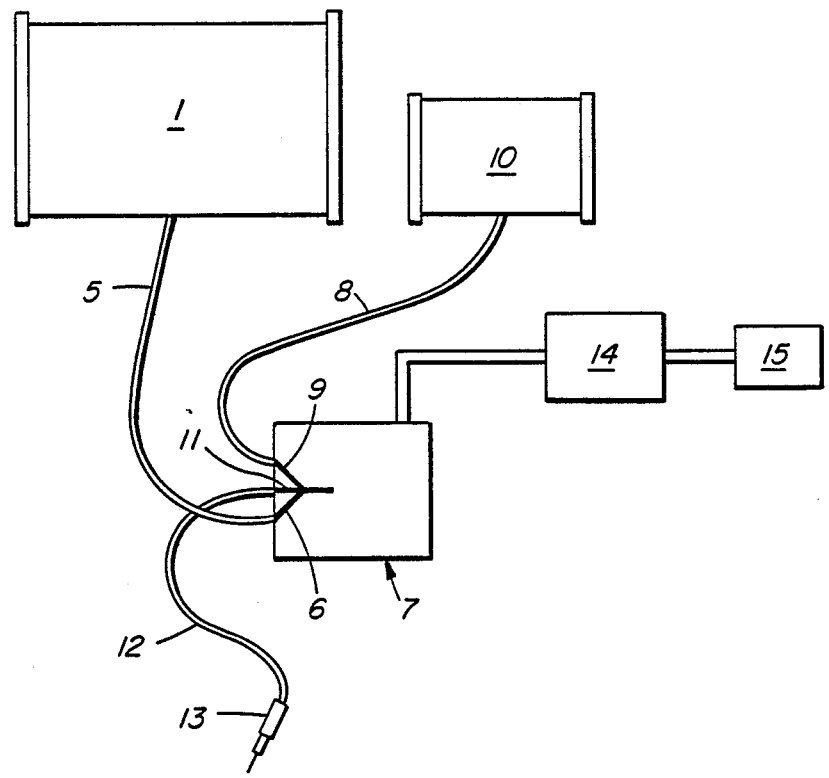
FIG. 1 is a sketch of an infusion pump according to the prior art.
Figure 2:
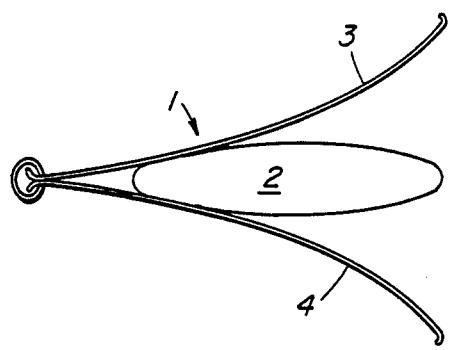
FIG. 2 is an enlarged view of the disposable medication bag of the embodiment of FIG. 1.
Figure 3:
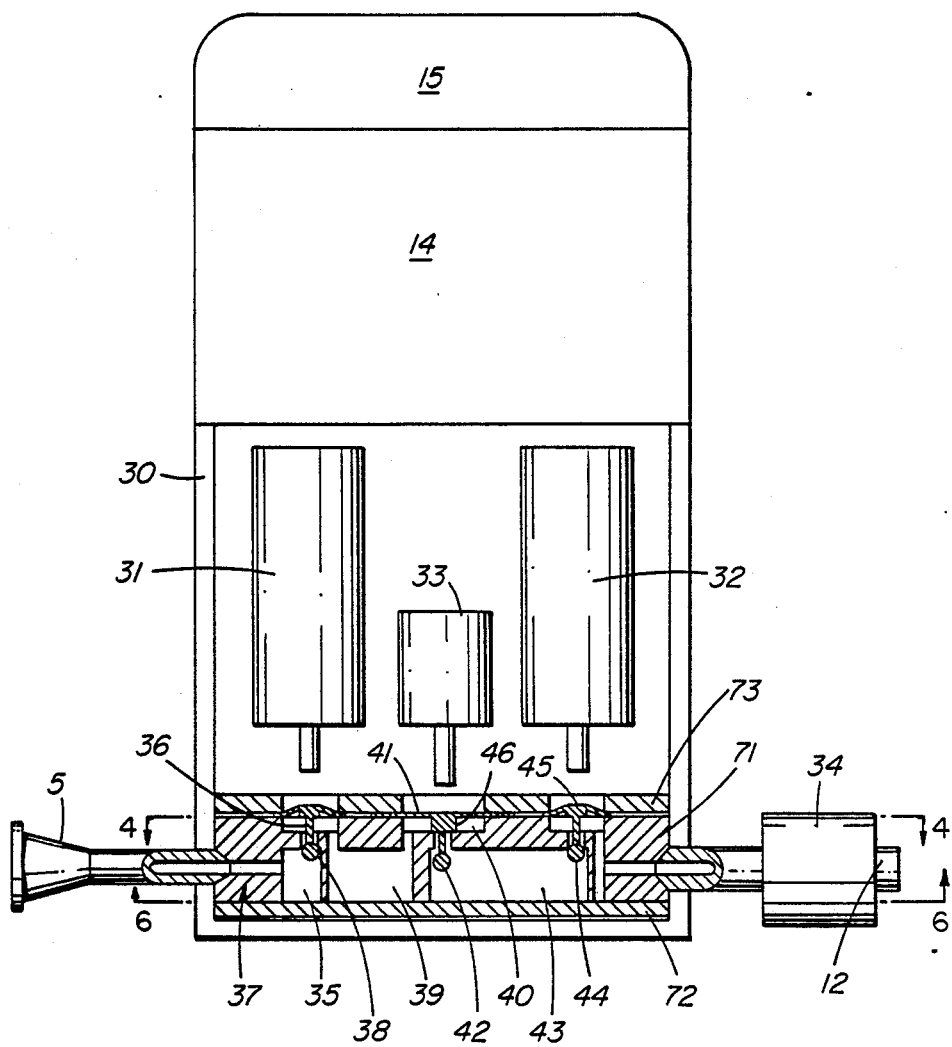
FIG. 3 is a cross sectional frontal view of the device of the present invention, showing the metering chambers but without the pressurized medication bag.
Figure 4:
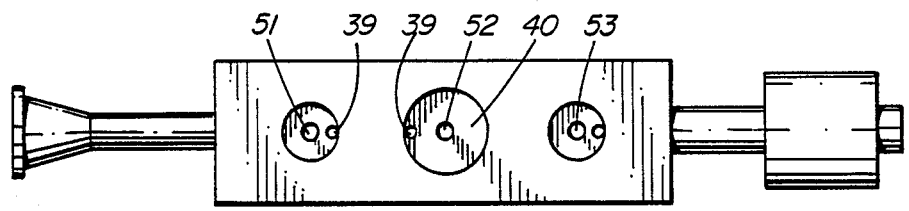
FIG. 4 is a plan view of the metering chambers of FIG. 3 taken along line 4—4.
Figure 5:
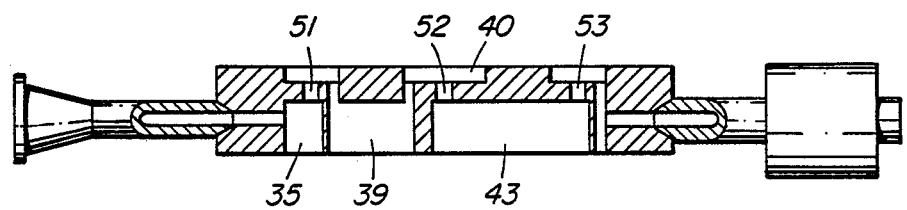
FIG. 5 is an enlarged side view of the central manifold section of the valve of FIG. 3.
Figure 6:
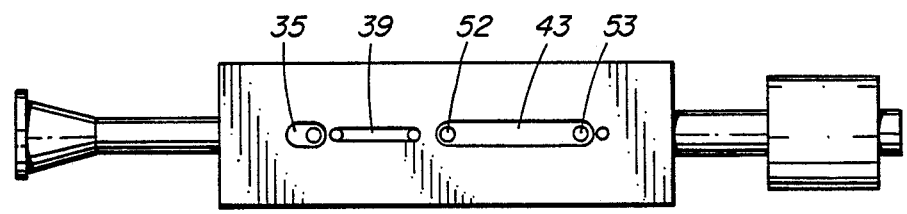
FIG. 6 is a bottom view taken along line 6—6 of FIG. 3.

Turning firstly to our prior device as described in U.S. Pat. No. 4,596,558, the operation of which is schematically illustrated in FIG. 1. In FIG. 1 there is shown a medication reservoir 1 comprising a disposable, sealed, flexible thermoplastic envelope 2 (as seen in FIG. 2) which is prefilled with a liquid medication to be dispensed. Pressure is applied to the medication envelope 2 by means of a pair of prestressed leaf springs 3,4 which are secured around envelope 2. The interior of envelope 2 is in fluid communication, via a flexible conduit 5, preferably a thermoplastic tube, with a port 6 of a three way valve 7 operated by a solenoid. A second flexible tube 8 fluidly interconnects a second port 9 of valve 7 to a dosage metering chamber 10 which is relatively smaller than reservoir 1. Chamber 10 also includes a disposable, sealed, flexible envelope which is under external pressure applied by opposed external leaf springs. The pressure in chamber 10 is always less than the pressure in envelope 2. A third port 11 of valve 7 is in fluid communication, via a third flexible tube 12 to a catheter 13 which may be subcutaneously or intravenously introduced into a patient. In the normal, unenergized condition the solenoid plunger of valve 7 is positioned so that port 11 is closed while ports 6 and 9 are open so that medication from reservoir 1 can flow into dosage metering chamber 10 which has a controllable volume. Upon energization of the solenoid in valve 7, by means of timer control 14 and power pack 15, port 6 is closed and ports 9 and 11 are opened, thereby permitting the medication under pressure in dosage metering chamber 10 to flow through the valve 7 and port 11 to the tube 12 and catheter 13. As the pressure in chamber 10 is always greater than the venous pressure, the entire contents of chamber 10 are discharged through catheter 13. Upon deenergization of the solenoid of valve 7, port 11 is again closed and port 6 is opened, thereby reopening the fluid passage ways between reservoir 1 and chamber 11, and as the pressure in reservoir 1 is always greater than the pressure in chamber 10, chamber 10 is refilled to its volumetric capacity. In the unlikely, but entirely possible, event of a streaming situation, perhaps with valve 7 in some intermediate position so that all three ports are at least partially open, the entire contents of reservoir 1 could flow directly to catheter 13 and the patient, resulting in a considerable overdose.

Various forms of alarms and emergency shut-off systems have been suggested but are relatively cumbersome and costly and the aim of the present invention is to provide a simple and inexpensive positively fail-safe operating system.

Reference is, therefore, now made to FIGS. 3-7 which illustrate one preferred embodiment of a simple, fail-safe, valve arrangement which can be used in a modified version of the ambulatory infusion pump described with reference to FIGS. 1 and 2. Contained within a housing 30 (shown in FIG. 3 with part of the cover removed) are the medication reservoir, under pressure as in the prior device, but not shown in FIG. 3: a valve 37 to be described in more detail hereinafter: an electronic control unit 14 powered by a power source 15: two solenoids 31, 32 controlled by controller 14 and powered by source 15, and a position sensor 33. A connector 34 is provided to connect the valve system to tube 12 so as to provide a continuous fluid flow path to a catheter (not shown). It will be appreciated that controller 14 could equally well be a mechanical controller and that the present invention is not limited to any particular type of controller.

Turning now more specifically to valve 37, it will be seen that an entry fluid passage 35 in fluid connection with inlet 5 is normally sealed by a resilient T-shaped valve element 36, having a bulbous tail 38. Element 36 is naturally and normally biased so that tail 38 seals the exit 51 from passage 35. A second fluid passage 39 is provided between valve element 36 and a medication volume metering chamber 40, which corresponds to the metering device 10 of the prior embodiment. A second resilient T-shaped valve element 41, having a bulbous tail 42, forms one wall of the chamber 40 with the bulbous tail 42 projecting into the orifice 52 of an exit passage 43. In the normal position, shoulders 46 on element 41 are biased into sealing engagement with the exit from chamber 40 Exit passage 43, which extends away from the exit from chamber 40, is normally blocked by the bulbous tail 44 of a third resilient T-shaped element 45, which is biased towards the sealing of the exit 53. Preferably, but not essentially, the valve elements 36, 41 and 45 are single piece resilient rubber mouldings. Valves 36 and 45 are generally identical and valve 41 is preferably of somewhat larger diameter with the T-piece rather thinner than the T-piece of valves 36 and 45.

In operation, valve 36 is naturally preloaded to draw bulbous end 38 upward into its associated flow path, thereby blocking passage of fluid from the reservoir into the valve 37. Similarly valve 45 is naturally preloaded to close the fluid passage out of valve 37. Furthermore, the larger central valve 41 is naturally preloaded to exhaust fluid out of the dosage chamber 40. Upon a signal from control unit 14, the inlet solenoid 31, which is preferably a bi-stable solenoid, is momentarily energized thereby driving its armature downward into contact with valve 36 which flexes and thus unseats bulbous end 38, opening the valve. Fluid can now enter the dosage chamber 40 from the main reservoir 1 via inlet 5. The thin rubber dome of valve 41 is distended upwardly until the displacement sensor 33 is triggered at the point when the chamber 40 contains a preselected volume of liquid. Sensor 33 is operatively coupled to control unit 14 and a signal is now sent to solenoid 31 to momentarily re-energize it, returning the solenoid armature to the up position and thus closing valve 36. Immediately following this, outlet solenoid 32, which is preferably a bi-stable solenoid, is momentarily energized, driving the solenoid downwardly to open valve 45. The distended central valve 41 can now return to its normal relaxed position, and its integral preload exhausts the accumulated dosage past the open valve 45 into the exit tube 12 and thence to the patient. After a sufficient time period, of the order of 2-10 seconds, to permit complete evacuation of the metered dose, the outlet solenoid 32 is again energized, driving its solenoid armature upwardly and thereby causing valve 45 to close. This completes one cycle of the system and the system remains dormant and essentially deenergized until the programmed control unit initiates another operating cycle.

The operation of valve arrangement 37 is essentially failsafe. Uncontrolled medication streaming to the patient can only happen if three simultaneous system failures occur, namely malfunction of both valves 36 simultaneously with a malfunction in an emergency cut off system integrally provided in valve 41 by tail 42. Valve 41 acts as a cut off in the following way, should valves 36 and 45 fail in the energized mode. The dosage chamber 40 will fill due to back pressure generated by downstream flow resistance and hence distend valve 41 upwardly so as to trigger the displacement sensor 33. Control unit 14 may be programmed to recognize the inappropriate filling of dosage chamber 40 with valves 36 and 45 open and signal an electrical pulse to solenoids 31 and 32 in an effort to close valves 36 and 45. Should this be unsuccessful for any reason, the dosage chamber 40 will fill beyond the preset limit as determined by sensor 33 and thus draw the bulbous tip 42 of T-shaped valve 41 upwardly into engagement with the orifice 52 of exit passage 43, thereby sealing off further flow. In effect the sealing of passage 43 by tip 42 is self energized and is maintained in the sealed position by the fluid pressure in the medication reservoir. The excessive movement of valve 41 will be monitored by sensor 33 and may be programmed to trigger an audible alarm signal and/or to operate the solenoid valves to close and even latch them.

Figure 7:
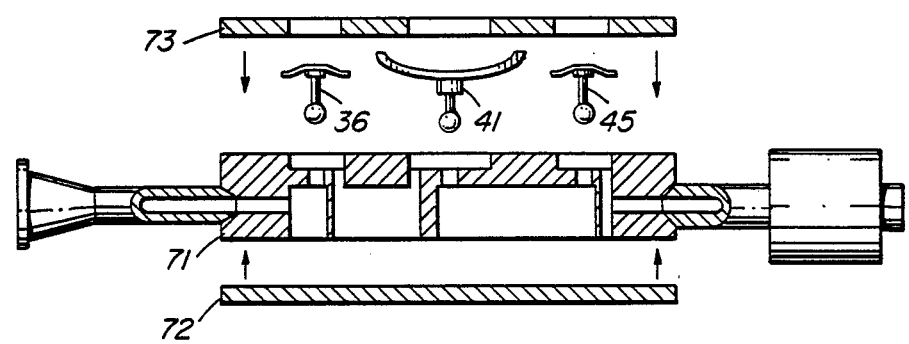
FIG. 7 is an exploded side view of the valve section of FIG. 3.

It will further be appreciated that the construction of valve 37 is relatively simple and can easily be fabricated, at low cost, by injection moulding in a plastics material, preferably a thermoplastic material such as high density polyethylene. There are essentially three body parts, as seen in FIG. 7, namely a manifold 71, a base plate 72 and a cover plate 73 which may be integrally formed and shape fitted together after insertion of the resilient valve elements 36, 41, and 45. It is not intended that valve 37 should be cleaned after use. The medication reservoir 1, conduit 5, valve 37, tube 12 and catheter 13 are considered to be disposable elements and any risk of contamination or loss of sterility from patient to patient is avoided.

We claim:

1. A pulsed liquid injection device comprising:
    liquid storage container for storing liquid under a pressure greater than that required for making an injection;
    a liquid metering chamber, having a predetermined capacity, for storing liquid under a pressure which is greater than that for making an injection but lower than the pressure in said first storage container;
    liquid dispensing means;
    a first liquid flow path between said storage container and said metering chamber;
    a second liquid flow path between said metering chamber and said liquid dispensing means;
    first valve means in said first liquid flow path movable between a first operating position in which said first liquid flow path is blocked and a second operating position which said first liquid flow path is open;
    second valve means in said second liquid flow path movable between a first operating position in which said second liquid flow path is blocked and a second operating position in which said second liquid flow path is open;
    timing means arranged, repeatedly at predetermined intervals, to (a) open said first valve means for just sufficient time to permit said liquid to flow into and fill said metering chamber and then return said first valve means to its first operating position, and subsequentially (b) open said second valve means for at least sufficient time to permit a predetermined volume of said liquid in said metering chamber to flow to said liquid dispensing means and then return said second valve means to its first operating position; and
    means intermediate said first and second valve means arranged to block said second liquid flow path in the event that liquid in excess of said predetermined capacity of said metering chamber is delivered thereto.

2. A pulsed liquid injection device as claimed in claim 1 including sensor means associated with said metering chamber to detect when said predetermined capacity has been reached and signal said timing means to return said first valve means to said first operating position.

3. A pulsed liquid injection device as claimed in claim 2 wherein said metering chamber includes flexible wall means movable between a first position out of contact with said sensor means, a second position in which said sensor means detects said predetermined capacity, and a third position in which said metering chamber contains more than said predetermined capacity.

4. A pulsed liquid injection device as claimed in claim 3 wherein said means intermediate said first and second valve means is operatively connected to said flexible wall means to thereby block said second liquid flow path when said flexible wall means is in said third position.

5. A pulsed liquid injection device as claimed in claim 4 wherein said sensor means provides said timing means with an emergency signal, when said flexible wall means is in said third position, to return both said first and second valve means to their respective first operating positions.

6. A pulsed liquid injection device as claimed in claim 1 wherein said timing means is an electrical timing means.

7. A pulsed liquid injection device as claimed in claim 6 wherein said electrical timing means include solenoid means operatively associated with each of said first and second valve means.

8. A pulsed liquid injection device as claimed in claim 1 wherein said first and second valve means comprise first and second flexible resilient planar members each having a bulbous member extending perpendicularly therefrom.

9. A pulsed liquid injection device as claimed in claim 8 wherein said resilient planar members comprise rubber planar members.

10. A pulsed liquid injection device as claimed in claim 9 wherein said planar members and said bulbous members are integrally moulded.

11. A pulsed liquid injection device as claimed in claim 10 wherein said planar members are preloaded to bias said bulbous members towards said first operating positions.

12. A pulsed liquid injection device as claimed in claim 1 wherein said means intermediate said first and second valve means comprises a third flexible resilient planar member having a bulbous member extending perpendicularly therefrom.

13. A pulsed liquid injection device as claimed in claim 12 wherein said third flexible planar member is a rubber member.

14. A pulsed liquid injection device as claimed in claim 13 wherein said third planar member and said bulbous member extending therefrom are integrally molded.

15. A valve arrangement adapted for addition to a pulsed liquid injection system, of which it then forms part, the arrangement comprising: a housing having a liquid flow path therethrough and containing a liquid metering chamber intermediate the ends thereof: first valve means in said flow path upstream of said metering chamber and second valve means in said flow path downstream of said metering chamber, said first and second valve means being operatively movable between respective first positions which block said flow path and second positions in which said flow path is open; and sensing means in said flow path operatively connected to third valve means arranged to block said liquid flow path in the event that in excess of a predetermined volume of liquid is exhausted from said metering chamber.

16. A valve arrangement as claimed in claim 15 wherein said first, second and third valve means comprise flexible resilient planar members each having a bulbous member extending perpendicularly therefrom.

17. A valve arrangement as claimed in claim 16 wherein said resilient planar members comprise rubber planar members.

18. A valve arrangement as claimed in claim 17 wherein said planar members and said bulbous members are integrally molded.

19. A pulsed liquid injection device as claimed in claim 18 including sensing means in at least one of said liquid flow paths operatively connected to third valve means between said storage container and said liquid dispensing means and arranged to block said liquid flow path in the event that in excess of a predetermined volume of liquid is exhausted from said metering chamber.

* * * * *